US005537994A

United States Patent [19]
Thornton

[11] Patent Number: 5,537,994
[45] Date of Patent: Jul. 23, 1996

[54] COMBINATION FACE MASK AND DENTAL DEVICE FOR IMPROVED BREATHING DURING SLEEP

[76] Inventor: W. Keith Thornton, 5524 Edlen, Dallas, Dallas County, Tex. 75220

[21] Appl. No.: 253,949

[22] Filed: Jun. 3, 1994

[51] Int. Cl.$^6$ .................................................. A61M 21/00
[52] U.S. Cl. .................. 128/204.18; 128/201.18; 128/205.25; 128/206.21; 128/207.18; 128/848
[58] Field of Search ..................................... 128/859, 860, 128/861, 862, 201.26, 203.29, 205.25, 206.21, 206.22, 206.24, 206.27, 206.28, 206.29, 207.11, 848, 204.18

[56] References Cited

U.S. PATENT DOCUMENTS

| | | |
|---|---|---|
| 746,869 | 12/1903 | Moulton . |
| 1,146,264 | 7/1915 | Kelly ........................................ 128/861 |
| 1,674,336 | 6/1928 | King . |
| 2,424,533 | 7/1947 | Faires ....................................... 128/136 |
| 2,521,039 | 9/1950 | Carpenter ................................ 128/136 |
| 2,531,222 | 11/1950 | Kesling ........................................ 32/14 |
| 2,590,118 | 3/1952 | Oddo, Jr. ................................. 128/136 |
| 2,833,278 | 5/1958 | Ross .......................................... 128/136 |
| 2,882,893 | 4/1959 | Godfroy ................................... 128/136 |
| 3,107,668 | 10/1963 | Thompson ............................... 128/136 |
| 3,124,129 | 3/1964 | Grossberg ................................ 128/862 |
| 3,434,470 | 3/1969 | Strickland ................................ 128/136 |
| 3,457,916 | 7/1969 | Wolicki .................................... 128/862 |
| 3,513,838 | 5/1970 | Foderick et al. ........................ 128/136 |
| 3,864,832 | 2/1975 | Carlson ....................................... 32/40 |
| 3,871,370 | 3/1975 | McDonald ................................ 128/136 |
| 4,016,650 | 4/1977 | Leusner et al. ............................ 32/17 |
| 4,114,614 | 9/1978 | Kesling .................................... 128/136 |
| 4,227,877 | 10/1980 | Tureaud et al. ............................ 433/37 |
| 4,304,227 | 12/1981 | Samelson ................................. 128/136 |
| 4,376,628 | 3/1983 | Aardse ........................................ 433/80 |
| 4,495,945 | 1/1985 | Liegner ................................ 128/200.26 |
| 4,553,549 | 11/1985 | Pope et al. ............................... 128/136 |
| 4,568,280 | 2/1986 | Ahlin ............................................ 433/6 |
| 4,569,342 | 2/1986 | von Nostitz ............................. 128/136 |
| 4,593,686 | 6/1986 | Lloyd et al. ............................. 128/136 |
| 4,655,213 | 4/1987 | Rapopost et al. .................... 128/205.25 |
| 4,799,500 | 1/1989 | Newbury ................................. 128/859 |
| 4,862,903 | 9/1989 | Campbell ................................ 128/861 |
| 4,901,737 | 2/1990 | Toone ...................................... 128/848 |
| 4,919,128 | 4/1990 | Kopala et al. ...................... 128/205.25 |
| 4,955,393 | 9/1990 | Adell ....................................... 128/859 |
| 5,003,994 | 4/1991 | Cook ....................................... 128/848 |
| 5,018,533 | 5/1991 | Hawkins ................................. 128/848 |
| 5,042,506 | 8/1991 | Liberati .................................. 128/848 |
| 5,056,534 | 10/1991 | Wright .................................... 128/848 |
| 5,092,346 | 3/1992 | Hays et al. ............................. 128/848 |
| 5,103,838 | 4/1992 | Yousif ..................................... 128/859 |
| 5,117,816 | 6/1992 | Shapiro et al. ...................... 128/200.24 |
| 5,313,960 | 5/1994 | Tomasi ................................... 128/859 |

FOREIGN PATENT DOCUMENTS

| | | | |
|---|---|---|---|
| 0312368 | 4/1989 | European Pat. Off. .......... | A61F 5/56 |
| 0359135 | 3/1990 | European Pat. Off. ........ | A63B 71/10 |
| 2320501 | 11/1974 | Germany ......................... | A61F 5/56 |
| 3707952 | 9/1988 | Germany ......................... | 128/205.25 |
| 1569129 | 6/1980 | United Kingdom ............. | A61F 5/56 |

Primary Examiner—Edgar S. Burr
Assistant Examiner—V. Srivastava
Attorney, Agent, or Firm—Baker & Botts

[57] ABSTRACT

A combination face mask and dental device for improved breathing during sleeping is provided in which a face mask (10) is connected through an air tube (14) to a gas supply system (16). The face mask (10) is connected through a connector (20) to a dental device (18).

9 Claims, 4 Drawing Sheets

COMBINATION FACE MASK AND DENTAL DEVICE FOR IMPROVED BREATHING DURING SLEEP

CROSS REFERENCES TO RELATED APPLICATIONS

This application is related to U.S. patent application Ser. No. 08/129,598, filed Sep. 29, 1993 and entitled APPARATUS FOR PREVENTION OF SNORING AND IMPROVED BREATHING DURING SLEEP.

TECHNICAL FIELD OF THE INVENTION

This invention relates generally to medical devices, and more particularly to a combination face mask and dental device for improved breathing during sleep.

BACKGROUND OF THE INVENTION

Many people experience difficulty in sleeping because of breathing problems. These problems may result in snoring, or the more serious condition of sleep apnea.

One treatment for serious sleep breathing disorders involves application of constant positive air pressure ("CPAP") to the patient. This CPAP is delivered through a face mask, nose mask, or nasal inserts and results in opening of the patient's breathing passageway. The CPAP pressure must be increased for more serious conditions. Face masks for delivering CPAP are commonly secured to the patient's head with an adjustable or elastic strap. As the patient moves during sleep, the face mask often shifts and unseats from the patient's face, resulting in a loss of pressure from the CPAP, or awakening of the patient.

Another treatment for sleep breathing disorders involves the use of dental devices for extending forward the lower jaw of the patient. These devices operate to more fully open the breathing passageway, thereby allowing for easier breathing, whether that breathing be through the nose or through the mouth. These dental devices treat snoring problems very well, but may not sufficiently treat more serious cases, such as some sleep apnea cases.

Therefore, a need has arisen for a device that will allow for more efficient treatment of breathing disorders during sleep, and which will assist in maintaining the proper seating of a CPAP face mask.

SUMMARY OF THE INVENTION

In accordance with the teachings of the present invention, a combination face mask and dental device is provided which significantly reduces or eliminates disadvantages and problems associated with prior art devices for treating breathing disorders during sleep.

In particular, a device for assisting breathing is provided in which a face mask is connected to a system for supplying gas to the face mask. A dental device is connected to the face mask. With such a system, the dental device serves as an anchor for the face mask. In a particular embodiment, the system for supplying gas is a constant positive air pressure system.

Furthermore, the dental device may comprise an upper arch that includes a post for causing a user's lower jaw to extend forward. The upper arch may be a custom mold of at least some of the user's upper teeth. Also, the upper arch may include a deformable material capable of being molded to as least some of the user's upper teeth.

In a particular embodiment, the dental device is connected to the face mask through a connector. The connector may include a support member coupled to the face mask at a first ball joint. The connector may also include a joining member coupled to the support member at a second ball joint, the joining member coupled to the dental device.

An important technical advantage of the present invention is the fact that a face mask is anchored by a dental device, thereby providing a more secure fit for the face mask.

Another important technical advantage of the present invention is the fact that a dental device may be used which causes the lower jaw to extend forward, thereby increasing the opening of the user's breathing passageway. This increased opening increases the effectiveness of treatment for sleep breathing disorders, such as sleep apnea.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

Figure 1:
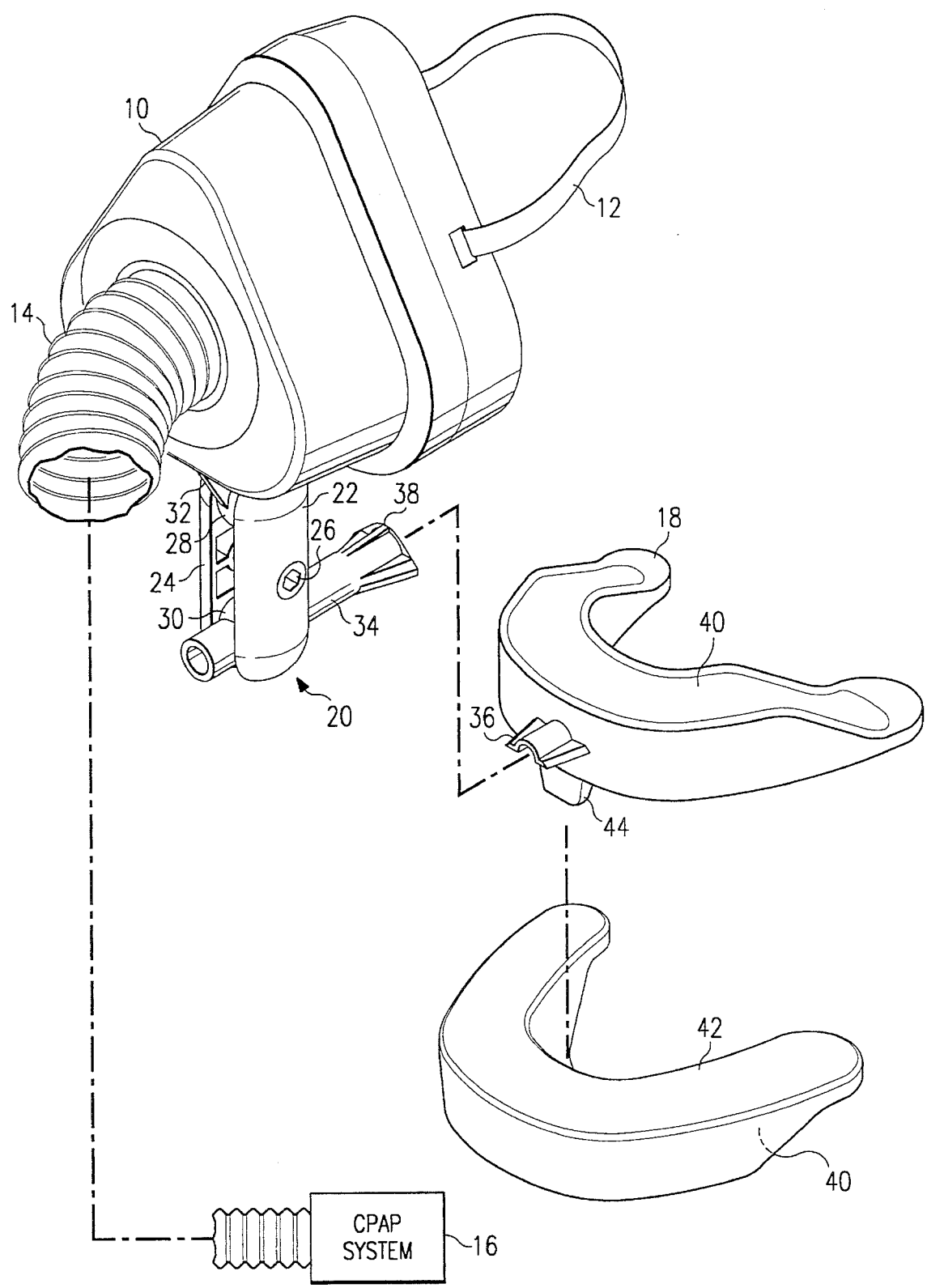
FIG. 1 illustrates a combination face mask and dental device according to the teachings of the present invention.

FIG. 1 illustrates a combination face mask and dental device according to the teachings of the present invention. As shown in FIG. 1, a face mask 10 is provided for fitting over a patient's nose. The particular face mask 10 shown in FIG. 1 is illustrative only, and any other face masks may be used without departing from the intended scope of the present invention. For example, the face mask 10 may fit over the patient's nose and mouth together, or mouth alone. Furthermore, the face mask 10 may be nasal inserts, or any device used to couple air to a patient. As shown in FIG. 1, face mask 10 may be secured to the patient's head with a strap 12. Strap 12 may be adjustable or elastic.

Face mask 10 is coupled through air tube 14 to CPAP system 16. CPAP system 16 provides constant positive air pressure to the patient through face mask 10. The pressure of the air delivered by CPAP system 16 depends upon the severity of the breathing disorder being treated. The more severe the disorder, the greater the pressure must be. In general, increasing the air pressure delivered by CPAP system 16 increases the opening of the breathing passageway. CPAP system 16 is shown as an example only. Other systems for delivering air at constant or varying pressures may also be used. Furthermore, any such systems may deliver any breathable gas, such as air or oxygen. It should be understood that the term "gas" used throughout this patent is meant to include air. Face mask 10 should be configured so as to allow air exhaled by the patient to be exhausted from the face mask 10.

As shown in FIG. 1, face mask 10 is connected to a dental device 18 through connector 20. Connector 20 includes support members 22 and 24 which are joined by tightener 26. For example, tightener 26 may be a tightening screw, a tightening bolt, or any other device for tightening. Support members 22 and 24 may be separate, or may be a single support member. Support members 22 and 24 communicate with a ball 28 and a ring 30. Ball 28 is connected to face mask 10 through a support 32. Ring 30 surrounds a joining member 34.

Joining member 34 attaches to dental device 18 at a connecting member 36 which is attached to dental device 18. End 38 of joining member 34 may connect with member 36 in any suitable fashion. For example, member 36 may be hollow and tapered as shown in FIG. 1, so that member 36 wedgedly engages in end 38. Similarly, end 38 may wedgedly engage with member 36. As another alternative, end 38 and member 36 may be connected with a fastener, such as a bolt, screw, or set pin, among others. Similarly, end 38 and member 36 may be bonded, as through a weld or adhesive. It should be understood that joining member 34 may be attached to dental device 18 in any suitable way.

Support members 22 and 24 in conjunction with ball 28 effectively form a universal ball joint, and thus support members 22 and 24 can freely move about ball 28. Similarly, ring 30 and support members 22 and 24 effectively form a universal ball joint, and thus joining member 34 can freely move up and down, and left and right, with respect to the patient.

The freedom of movement allowed by ball 28 and ring 30 allow for the dental device 18 and the face mask 10 to be comfortably and effectively fitted. Once they are so fitted, tightener 26 is tightened so as to maintain this comfortable and effective relationship between the face mask 10 and the dental device 18.

During use, the dental device 18 will be securely in place in the patient's mouth. Because it is connected to face mask 10 through connector 20, dental device 18 acts as an anchor, maintaining the placement and fit of face mask 10. This anchoring effect provides a significant advantage over prior art use of only a face mask, as use of only a face mask often results in unseating of the face mask during sleep.

As shown in FIG. 1, dental device 18 is an upper arch. Dental device 18 includes a deformable material 40 bonded to the device 18 and used for forming a mold of the patient's teeth for proper fitting. A suitable material for deformable material 40 is the ethylene-vinyl acetate copolymer resin sold under the registered trademark ELVAX. Any other suitable deformable materials may also be used. Typically, with a material such as ELVAX, the material 40 is heated to a temperature of about 150° F., through a microwave oven or by heating in hot water, for example, so as to place the material 40 in its deformable state. A patient then inserts the dental device and bites down, thereby deforming the material 40 into the shape of the patient's teeth. The dental device is then removed and allowed to cool, thereby setting the material 40 into a mold of the patient's teeth.

Also shown in FIG. 1 is a lower arch 42. Lower arch 42 may also include a deformable material 40. In a preferred embodiment, dental device 18 includes a downwardly extending post 44 which contacts lower arch 42 as shown in FIG. 1. This contacting forces the lower arch 42, and consequently the patient's lower jaw, forward, thereby opening the breathing passageway. By using the dental device shown in FIG. 1, the effectiveness of sleep breathing disorder treatments are enhanced, since not only is the CPAP treatment being applied, but so is the dental device treatment which increases the opening of the breathing passageway.

By using the dental device 18 shown in FIG. 1, the breathing passageway is opened more than normal, and thus CPAP system 16 need not deliver gas at as high a pressure as would be necessary without use of the dental device shown in FIG. 1. This provides a significant advantage over the use of CPAP systems alone.

Figure 2:
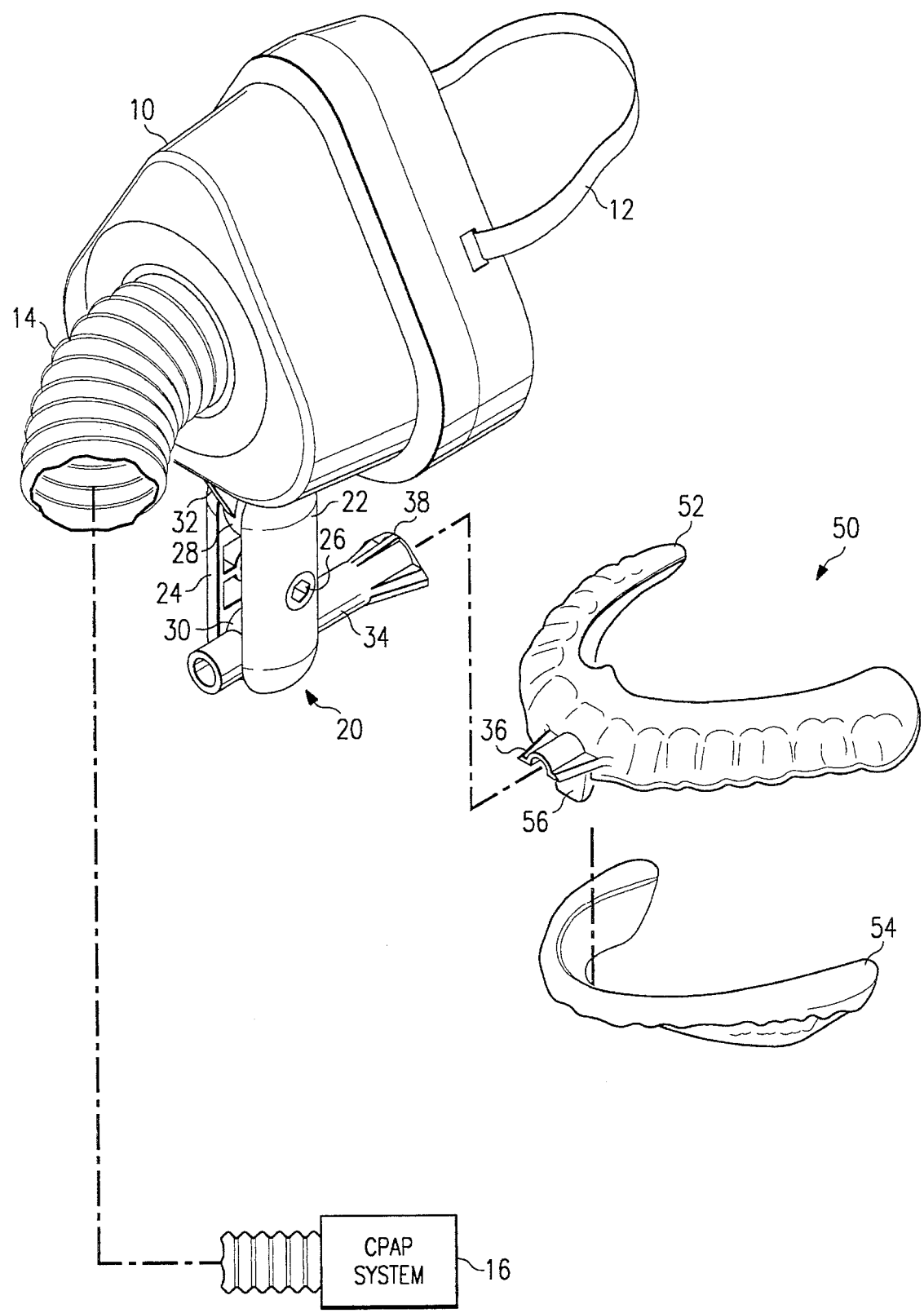
FIG. 2 illustrates an alternative embodiment of a dental device according to the teachings of the present invention.

The particular dental device shown in FIG. 1 is exemplary only, and other dental devices may be used without departing from the intended scope of the present invention. For example, the dental device shown in FIG. 1 is customized by a patient. However, as shown in FIG. 2, a dental device 50 molded from the patient's teeth by a dental professional may also be used. Dental device 50 includes upper arch 52, lower arch 54, and post 56. As another example, the lower arches 42 and 54 shown in FIGS. 1 and 2 need not be included. Without the lower arches, the posts 44 and 56 would contact the patient's teeth and gum. Examples of other suitable dental devices are described throughout U.S. patent application Ser. No. 08/129,598, entitled APPARATUS FOR PREVENTION OF SNORING AND IMPROVED BREATHING DURING SLEEP, which is herein incorporated by reference.

Moreover, although the preferred embodiment of the present invention is with a dental device that more fully opens the breathing passageway of the patient, dental devices that do not perform this function may also be used. As discussed above, one of the advantages of the present invention is that the dental device is used to anchor the face mask 10. Thus, any dental device that performs the anchoring function is contemplated by the present invention. As an example, a lower arch alone could be used to connect to face mask 10. Furthermore, dental devices not shaped as arches could also be used. Indeed, the term dental device is meant to include any oral appliance which can serve as an anchor for face mask 10.

Figure 3:
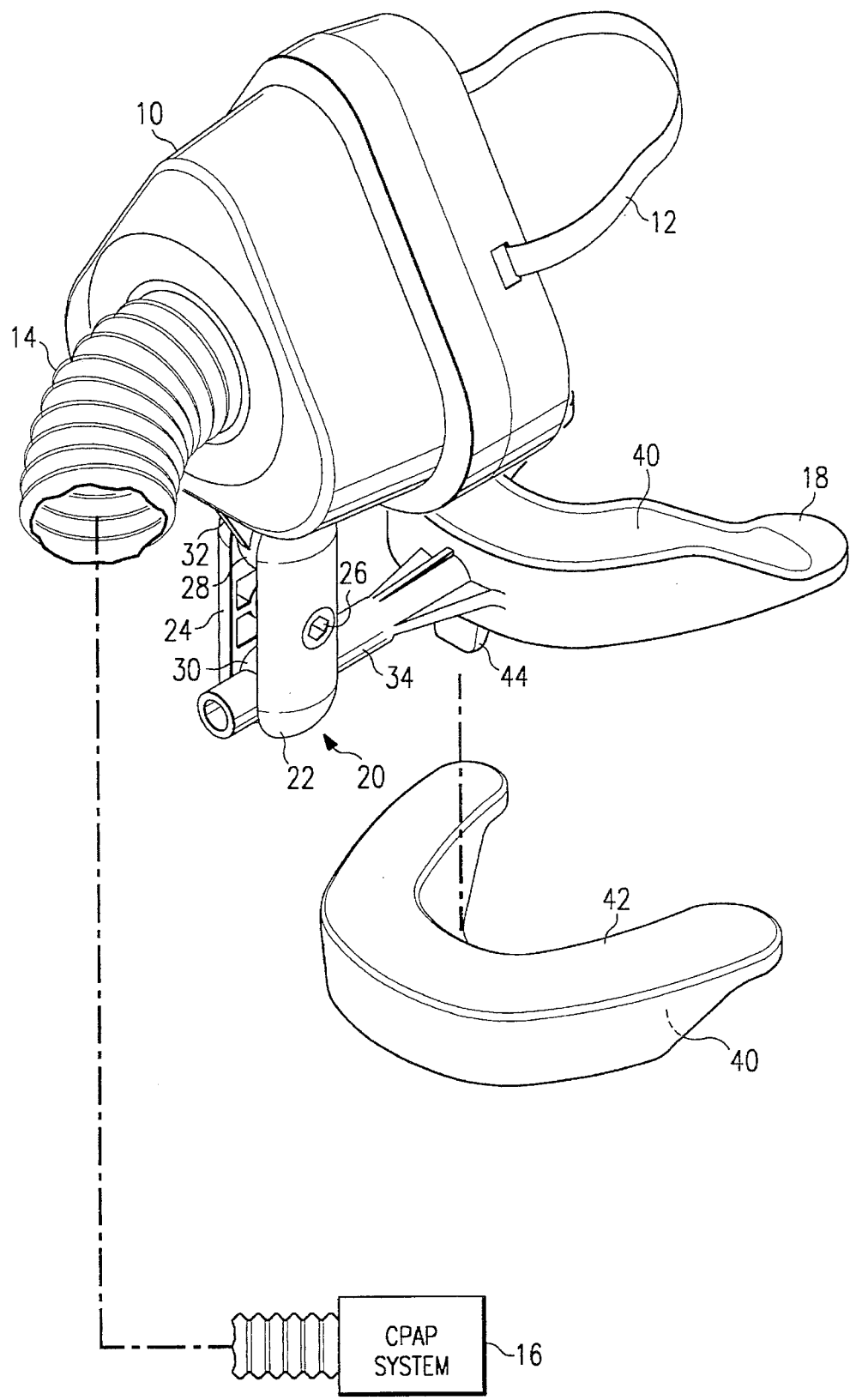
FIG. 3 illustrates another embodiment of a combination face mask and dental device according to the teachings of the present invention.

FIG. 3 illustrates another embodiment of the present invention in which the joining member 34 is directly connected to dental device 18. With this embodiment, no connecting is required between the joining member 34 and the member 36 shown in FIG. 1.

Figure 4:
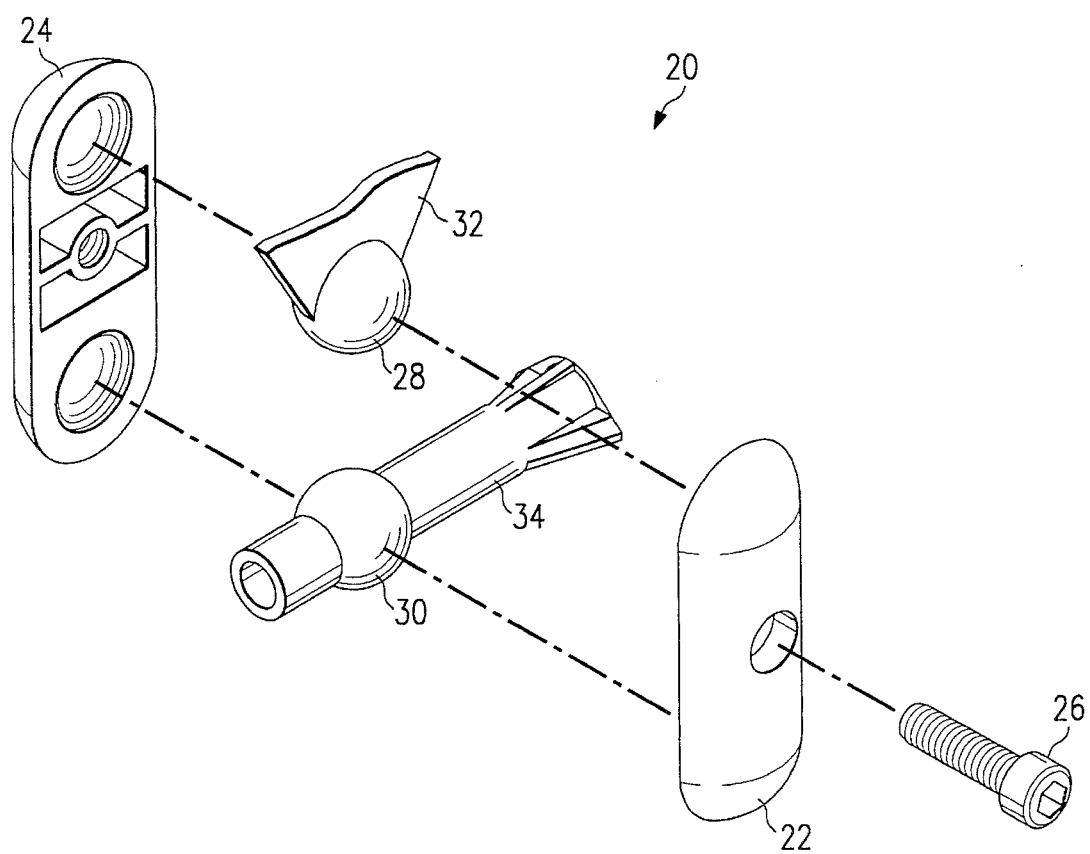
FIG. 4 illustrates an exploded view of an embodiment for a connection between a face mask and dental device according to the teachings of the present invention.

FIG. 4 illustrates an exploded view of connector 20. As shown in FIG. 4, support members 22 are joined by tightener 26. Support members 22, 24 are formed, as shown in FIG. 4, so as to provide seats for ball 28 and ring 30, respectively. Ball 28 is fastened to mask 10 through support 32. Support 32 may be fastened to mask 10 in any suitable fashion, such as by welding or bonding, or through the use of fasteners, such as brads, pins, screws, and bolts, for example. The connector 20 may be formed of any suitable material, such as plastic or metal. It should be understood that the particular connector 20 shown is exemplary, and other connectors may also be used. For example, connectors that do not allow movement, or connectors that allow less or more movement than connector 20, may also be used without departing from the intended scope of this invention.

In summary, a combination face mask and dental device is provided in which the dental device is connected to the face mask, and acts as an anchor to secure the position and seating of the face mask. The face mask is connected to a CPAP system for providing gas to a patient, thereby opening the patient's breathing passageway. Furthermore, the dental device may include the capability of extending the lower jaw forward, so as to open the patient's breathing passageway, thereby increasing the efficiency of treatment for breathing disorders during sleeping.

Although the present invention has been described in detail, it should be understood that various modifications, substitutions, or alterations can be made without departing from the intended scope as defined by the appended claims.

What is claimed is:

1. A device for assisting breathing, comprising:

a face mask;

a system for supplying gas to said face mask; and a dental device adjustably connected to said face mask;

a connector for connecting said dental device to said face mask, wherein said connector comprises:

a support member, having a fist ball joint and a second ball joint, coupled to said face mask at said first ball joint; and a joining member coupled to said support member at said second ball joint, said joining member coupled to said dental device.

2. The device of claim 1, wherein said support member comprises first and second individual support members.

3. A device for assisting breathing, comprising:

a face mask;

a system for supplying gas to said face mask;

a support member, having a first ball joint and a second ball joint, coupled to said face mask at said first bail joint;

a joining member coupled to said support member at said second ball joint; and an upper arch coupled to said joining member, said upper arch including a post for causing a user's lower jaw to extend forward.

4. The device of claim 3, wherein said support member comprises first and second individual support members.

5. The device of claim 3, wherein said system for supplying gas comprises a constant positive air pressure system.

6. The device of claim 3, and further comprising a lower arch.

7. The device of claim 3, wherein said upper arch comprises a custom mold of at least some of a user's upper teeth.

8. The device of claim 7, wherein said upper arch includes a deformable material capable of being molded to at least some of a user's upper teeth.

9. A device for assisting breathing, comprising:

a face mask operable to deliver air to the nose of a user, the face mask operable to prevent the device from delivering air to the lips of the user;

a system for supplying gas to said face mask;

a dental device adjustably connected to said face mask; and a connector for connecting said dental device to said face mask, wherein said connector comprises:

a support member, having a first ball joint and a second ball joint, coupled to said face mask at said first ball joint; and a joining member coupled to said support member at said second ball joint, said joining member coupled to said dental device.

* * * * *